United States Patent
Hynes

(10) Patent No.: US 8,927,759 B2
(45) Date of Patent: Jan. 6, 2015

(54) METHOD FOR PRODUCING 2-CYANOACETIC ACID ANHYDRIDE AND FURTHER REACTION PRODUCTS THEREOF

(71) Applicant: Loctite (R&D) Limited Ltd., Dublin (IE)

(72) Inventor: Stephen Hynes, Dublin (IE)

(73) Assignee: Henkel IP & Holding GmbH, Duesseldorf (DE)

( * ) Notice: Subject to any disclaimer, the term of this patent is extended or adjusted under 35 U.S.C. 154(b) by 171 days.

(21) Appl. No.: 13/744,494

(22) Filed: Jan. 18, 2013

(65) Prior Publication Data

US 2013/0131370 A1    May 23, 2013

(30) Foreign Application Priority Data

Jul. 23, 2010 (EP) .................................... 10170562

(51) Int. Cl.
   *C07C 253/30*    (2006.01)
(52) U.S. Cl.
   CPC .................................. *C07C 253/30* (2013.01)
   USPC ........................................................ 558/442
(58) Field of Classification Search
   USPC ........................................................ 558/442
   See application file for complete search history.

(56) References Cited

U.S. PATENT DOCUMENTS

| 4,063,882 A * | 12/1977 | Steiner .............................. 8/527 |
| 5,756,807 A | 5/1998 | Grund et al. |
| 6,700,010 B1 | 3/2004 | Hanselmann et al. |

FOREIGN PATENT DOCUMENTS

| WO | 9201296 | 1/1992 |
| WO | 2006021282 | 3/2006 |

OTHER PUBLICATIONS

International Search Report issued in connection with International Patent Application No. PCT/EP2011/061918 mailed on Oct. 11, 2011.
Inoue, Masashi et al: "The influence of electron delocalization on the rate constants for competing BAc2 and E1cb ester hydrolyses".
Khalil, Khaled D. et al: "Studies with enaminonitriles: synthesis of 3-aroyl- and 3-heteroaroylpyrazolo[1,5-a] pyrimidines".

* cited by examiner

*Primary Examiner* — Joseph Kosack
(74) *Attorney, Agent, or Firm* — Steven C. Bauman; James E. Piotrowski

(57) ABSTRACT

The present invention relates to a process for producing 2-cyanoacetic acid anhydride, comprising the steps of a) preparing a reaction mixture, containing as reactants 2-cyanoacetic acid, and at least one $C_{4-20}$ carboxylic acid anhydride in at least one organic solvent, wherein the molar ratio of 2-cyanoacetic acid to $C_{4-20}$ carboxylic acid anhydride in said reaction mixture is greater than 1.5:1, and b) subjecting the reaction mixture to a temperature of 0° C. to 100° C. to form 2-cyanoacetic acid anhydride. The present invention also relates to process for producing 2-cyanoacetic acid esters, 2-cyanoacetic acid amides and/or 2-cyanoacetic acid thioesters from 2-cyanoacetic acid anhydride.

15 Claims, No Drawings

METHOD FOR PRODUCING 2-CYANOACETIC ACID ANHYDRIDE AND FURTHER REACTION PRODUCTS THEREOF

The present invention relates to a process for producing 2-cyanoacetic acid anhydride. Furthermore, the present invention relates to a process for producing 2-cyanoacetic acid esters, 2-cyanoacetic acid amides and/or 2-cyanoacetic acid thioesters from 2-cyanoacetic acid anhydride.

Cyanoacrylate adhesives are known for their fast adhesion and ability to bond a wide variety of substrates.

They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and a 2-cyanoacetic acid ester with a basic catalyst. During the reaction, cyanoacrylate monomer forms and polymerises in situ to a prepolymer. The prepolymer is subsequently thermally cracked or depolymerised, yielding cyanoacrylate monomer.

This approach has remained essentially the same over time, though various improvements and variants have been introduced.

A variety of processes for the production of 2-cyanoacetic acid esters are known, some of which are described below.

For instance, WO 1992/01296 A1 describes the oxidation of partially oxidized propionitriles (e.g. cyano-acetaldehyde or acetals thereof) by means of oxygen or other oxidants in the presence of catalysts such as iron chloride or palladium chloride, cyanoacetic acid likewise being formed first, which then has to be converted into a cyanoacetic acid ester by acid-catalyzed esterification with the appropriate alcohol.

U.S. Pat. No. 6,700,010 B1 discloses a process for the preparation of cyanoacetic acid esters, comprising the step of oxidizing alkoxypropionitriles by using oxygen or an oxygen-forming reagent in the presence of a catalyst based on lead or one of the transition metals.

Other processes rely on transesterification reactions of 2-cyanoacetic acid. For example U.S. Pat. No. 5,756,807 teaches a process for preparing alkyl 2-cyanoacetates by reacting cyanoacetic acid in aqueous medium with an alcohol $R(OH)_n$, wherein the esterification is carried out in the presence of an inert entrainer other than water, and, during the reaction, water and entrainer are distilled out under atmospheric or reduced pressure. The described method normally requires high reaction temperatures and long reaction times and often unwanted by-products, such as dialkyl malonates are formed.

Notwithstanding the state of technology, it would be desirable to provide an alternative method for the production of 2-cyanoacetic acid esters and derivatives thereof, like 2-cyanoacetic acid amides or 2-cyanoacetic acid thioesters. It would be particularly desirable to provide a method for the selective production of the aforementioned compounds, which is cost-efficient, uses cheap starting materials, mild conditions and affords excellent yields.

The present invention provides a method for the selective production of 2-cyanoacetic acid esters and derivatives thereof, which is based on the selective formation of 2-cyanoacetic acid anhydride in an organic solvent.

Therefore, one aspect of the present invention is a process for producing 2-cyanoacetic acid anhydride (first process), comprising the steps of a) preparing a reaction mixture, containing as reactants 2-cyanoacetic acid, and at least one $C_{4-20}$ carboxylic acid anhydride in at least one organic solvent, wherein the molar ratio of 2-cyanoacetic acid to $C_{4-20}$ carboxylic acid anhydride in said reaction mixture is greater than 1.5:1; and b) subjecting the reaction mixture to a temperature of 0° C. to 100° C. to form 2-cyanoacetic acid anhydride.

By using 2-cyanoacetic acid and at least one $C_{4-20}$ carboxylic acid anhydride as cheap starting materials in a molar ratio of greater than 1.5:1, 2-cyanoacetic acid anhydride can be produced in a cost-efficient way under mild conditions.

Another aspect of the present invention is a process for producing 2-cyanoacetic acid esters, 2-cyanoacetic acid amides and/or 2-cyanoacetic acid thioesters (second process), comprising the steps of i) carrying out the first process of the present invention to prepare a reaction mixture containing 2-cyanoacetic acid anhydride in an organic solvent, ii) adding at least one reagent to the reaction mixture, wherein said reagent is selected from the group consisting of hydroxyl-containing compounds, amine-containing compounds, and thiol-containing compounds, and iii) subjecting said mixture to a temperature of −20° C. to 80° C. to form 2-cyanoacetic acid esters, 2-cyanoacetic acid amides and/or 2-cyanoacetic acid thioesters.

As noted above, one aspect of the present invention is a first process for producing 2-cyanoacetic acid anhydride, comprising the steps of a) preparing a reaction mixture, containing as reactants 2-cyanoacetic acid, and at least one $C_{4-20}$ carboxylic acid anhydride in at least one organic solvent, wherein the molar ratio of 2-cyanoacetic acid to $C_{4-20}$ carboxylic acid anhydride in said reaction mixture is greater than 1.5:1; and b) subjecting the reaction mixture to a temperature of 0° C. to 100° C. to form 2-cyanoacetic acid anhydride.

The molar ratio of 2-cyanoacetic acid to $C_{4-20}$ carboxylic acid anhydride of more than 1.5:1 is crucial for the selective formation of 2-cyanoacetic acid anhydride in the first process of the present invention. By using 2-cyanoacetic acid and $C_{4-20}$ carboxylic acid in a molar ratio of more than 1.5:1, 2-cyanoacetic acid anhydride is produced in high yields and the formation of unwanted by-products, like the mixed anhydride of 2-cyanoacetic acid and $C_{4-20}$ carboxylic acid is reduced.

In particular, it is preferred that the molar ratio of 2-cyanoacetic acid to $C_{4-20}$ carboxylic acid anhydride in the reaction mixture used in the process of the present invention is from 2:1 to 3:1. By preparing a reaction mixture containing the reactants in a molar ratio from 2:1 to 3:1, the selectivity of the formation of 2-cyanoacetic acid anhydride in the first process of the present invention can be increased significantly, which means that in some embodiments of the present invention the desired main product 2-cyanoacetic acid anhydride can be obtained in a molar excess of greater than 5:1, more preferably of greater than 7:1, and most preferably of greater than 9:1 over the mixed anhydride of 2-cyanoacetic acid and $C_{4-20}$ carboxylic acid as an undesired by-product of the inventive process.

Normally, it is undesired to use 2-cyanoacetic acid to $C_{4-20}$ carboxylic acid anhydride in a molar ratio of more than 3:1, because the excess of 2-cyanoacetic acid is difficult to remove and an incomplete removal prior to the addition of the at least one reagent in the second process of the present invention could cause the formation of undesired by-products.

To obtain the highest selectivity in the inventive process of producing of 2-cyanoacetic acid anhydride, it is preferred that the molar ratio of 2-cyanoacetic acid to $C_{4-20}$ carboxylic acid anhydride in the reaction mixture of the present invention is in the range of 2:1 to 2.5:1, preferably in the range of 2:1 to 2.4:1, and more preferably in the range of 2.1:1 to 2.3:1.

The term "$C_{4-20}$ carboxylic acid anhydride" as used in the present invention, refers to a symmetrical or mixed anhydride of carboxylic acids, wherein said anhydride comprises the total number of 4 to 20 carbon atoms.

The term "symmetrical anhydride", as used in the present invention, refers to an anhydride of formula R—C(O)O—C(O)—R', wherein the residues R and R' are identical, whereas the term "mixed anhydride" refers to an anhydride of formula R—C(O)O—C(O)—R', where the residues R and R' are different.

In a preferred embodiment of the present invention the $C_{4-20}$ carboxylic acid anhydride is a symmetrical $C_{4-20}$ carboxylic acid anhydride. The use of symmetrical $C_{4-20}$ carboxylic acid anhydrides as reactants in the first process of the present invention is advantageous, because the symmetrical structure of said anhydride limits the number of possible side products, such as the number of mixed anhydrides of 2-cyanoacetic acids and $C_{4-20}$ carboxylic acids, which can be formed in the course of the first process.

Suitable $C_{4-20}$ carboxylic acid anhydrides can be selected from symmetrical carboxylic acid anhydrides of formula (I),

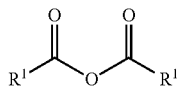

formula (I)

wherein $R^1$ represents, $C_{1-9}$-halogenoalkyl, or represents phenyl which is substituted by at least one substituent selected from fluorine, chlorine, bromine, cyano and/or nitro.

As used herein, the term "$C_{1-9}$ halogenoalkyl" refers to a $C_{1-9}$ alkyl group substituted by one or more halogen atoms, wherein the term "$C_{1-9}$ alkyl" refers to an aliphatic hydrocarbon group which may be straight, or branched having 1 to 9 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. Halogenoalkyl groups include notably perhalogenoalkyl groups, such as perfluoralkyl groups of formula $C_nF_{2n+1}$, wherein n is an integer from 1 to 9. Examples of preferred halogenalkyl groups include trifluoromethyl ($CF_3$).

The reactivity of the symmetrical $C_{4-20}$ carboxylic acid anhydrides of formula (I) can be simply controlled by varying the steric bulk and electronic nature of residue $R^1$. By using perhalogenoalkyl groups as residue $R^1$ the inventive process can be realized at relatively low temperatures of less than 50° C., preferably at a temperature from 10° C. to 40° C., such as a temperature from 15° C. to 35° C.

Preferred carboxylic acid anhydrides of formula (I), comprising perhalogenoalkyl groups are selected from compounds of formula (III),

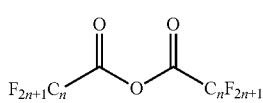

formula (III)

wherein each n, independently, is an integer from 1 to 10, preferably from 1 to 9 or from 1 to 5, and more preferably from 1 to 3.

In a preferred embodiment of the present invention, the $C_{4-20}$ carboxylic acid anhydride is trifluoroacetic acid anhydride (n=1). Trifluoroacetic acid anhydride is easily commercially available and allows the selective production of the desired product 2-cyanoacetic acid anhydride in a molar excess of greater than 6:1, more preferably of greater than 7:1, and most preferably of greater than 9:1 over the mixed anhydride of 2-cyanoacetic acid and trifluoroacetic acid as an undesired by-product of the first process.

To minimize the decomposition of the $C_{4-20}$ carboxylic acid anhydride and the formation of undesired by-products, it is preferred that the first process of the present invention is carried out under inert gas and/or under a dry atmosphere, wherein the term "dry atmosphere" refers to an atmosphere, which comprises less than 0.1 g/m³ of water at 20° C. and 1013 mbar.

As noted above, the reaction temperature of the first process of the present invention is in the range of 0° C. to 100° C., preferably in the range of 10° C. to 50° C., and more preferably in the range of 15° C. to 35° C. Depending on the reactivity of the reactants used in the first process of the present invention, the reaction time can vary, e.g. from 30 seconds to 96 hours, wherein reaction times of 2 hours to 30 hours, such as reaction times of 3 hours to 10 hours are preferred. By using trifluoroacetic acid anhydride as a reactant in the first process of the present invention, said process can be carried out under very mild conditions, e.g. at a reaction temperature of less than 50° C. in short time periods of less than 10 hours.

In principle the first process of the present invention can be carried out in a continuous or batch manner. If the reaction is carried out in a batch mode, then the reaction mixture is preferably prepared by mixing 2-cyanoacetic acid, at least one $C_{4-20}$ carboxylic acid anhydride, and at least one organic solvent in a reactor.

The reactor can be cooled or heated from inside or preferably from outside and/or can be equipped with a stirring device. Suitable stirring devices include anchor stirrers, propeller stirrers, cross-blade stirrers, and Mig stirrers or combinations thereof.

In an alternative embodiment, the first process of the present invention is carried out continuously in a flow-through reactor, wherein the reaction mixture flows continuously through the flow-through reactor.

"Continuously" is hereby understood to mean as usual a reaction mode, in which the reaction mixture flows through the reactor in at least such a period of time that a total volume of reaction medium that is large in comparison with the internal volume of the reactor itself has flowed through the reactor, before the flow of reaction medium is discontinued. "Large" in this context means: "at least twice as large". Naturally, a continuously operated reaction of this type also has a beginning and an end.

In this continuous process in a flow-through reactor it is possible for the reactor to have a plurality of heating or cooling zones. The different heating or cooling zones can be differently heated or cooled for example.

In one embodiment, the first process of the present invention comprises the additional step c) of isolating the formed 2-cyanoacetic acid anhydride by a process selected from the group consisting of extraction, crystallization, chromatography, distillation and co-distillation and combinations thereof.

However, it is one particular advantage of the present invention that normally it is not required to isolate the formed 2-cyanoacetic acid anhydride, because the first process of the present invention yields a stable solution of 2-cyanoacetic acid anhydride in an organic solvent. The stable solution can be stored under moisture free conditions (concentration of water of less than 0.1 g/m³ at 20° C. and 1013 mbar) for 1 to 30 days at a temperature of less than 25° C. without observing any major degradation, which means that less than 5% of all molecules of the formed 2-cyanoacetic acid anhydride are converted into their degradation products within the storage time given above.

The reaction mixture of the first process, containing 2-cyanoacetic acid anhydride in an organic solvent, can be directly used in another process (second process) without any further purification and/or stabilization step. By adding suitable hydroxyl-containing compounds, amine-containing compounds, and/or thiol-containing compounds to said reaction mixture, further reaction products, such as 2-cyanoacetic acid esters, 2-cyanoacetic acid amides and/or 2-cyanoacetic acid thioesters can be obtained.

Therefore, another aspect of the present invention is a process (second process) for producing 2-cyanoacetic acid esters, 2-cyanoacetic acid amides and/or 2-cyanoacetic acid thioesters, comprising the steps of i) carrying out the first process of the present invention to prepare a reaction mixture containing 2-cyanoacetic acid anhydride in an organic solvent, ii) adding at least one reagent to the reaction mixture, wherein said reagent is selected from the group consisting of hydroxyl-containing compounds, amine-containing compounds, and thiol-containing compounds, and iii) subjecting said mixture to a temperature of −20° C. to 80° C. to form 2-cyanoacetic acid esters, 2-cyanoacetic acid amides and/or 2-cyanoacetic acid thioesters.

As noted above, the second process of the present invention comprises as step i) the process for producing 2-cyanoacetic acid anhydride (first process) of the present invention. After carrying out the first process of the present invention as step i) of the second process of the present invention at least one suitable reagent is added in step ii) of the second process of the present invention to form 2-cyanoacetic acid esters, 2-cyanoacetic acid amides and/or 2-cyanoacetic acid thioesters.

As mentioned above, all features disclosed for the first process of the present invention also apply to step i) of the second process of the present invention.

The term "hydroxyl-containing compound", as used in the present invention, refers to any organic compound which comprises at least one hydroxyl group, wherein said compound is capable of reacting with 2-cyanoacetic acid anhydride.

The term "amine-containing compound", as used in the present invention, refers to any organic compound that comprises at least one primary or secondary amino group, wherein said compound is capable of reacting with 2-cyanoacetic acid anhydride.

The term "thiol-containing compound", as used in the present invention, refers to any organic compound which comprises at least one thiol group, wherein said compound is capable of reacting with 2-cyanoacetic acid anhydride.

Preferred hydroxyl-containing compounds include hydroxyl-containing oligomers or polymers, such as hydroxyl-group containing polyurethanes, monohydric alcohols and/or polyhydric alcohols.

The term "monohydric alcohol", as used in the present invention, refers to alcohols, comprising one hydroxyl groups. The term "polyhydric alcohol", as used in the present invention refers to alcohols, comprising at least two hydroxyl groups, such as alcohols comprising two, three or four hydroxyl groups.

In one embodiment of the present invention the at least one reagent is a monohydric or dihydric primary alcohol. Primary alcohols are preferred, because these compounds exhibit a high reactivity and are easily commercially available.

Preferred monohydric or dihydric primary alcohols include compounds of general formula (II), $$[HO{-}]_n R^2 \quad \text{formula (II)}$$

wherein n is 1 or 2 and $R^2$ stands for $C_{1-40}$ alkyl (for n=1), $C_{3-40}$ alkenyl (for n=1), $C_{3-40}$ cycloalkyl (for n=1), $C_{6-40}$ aryl (for n=1), $C_{7-40}$ aralkyl (for n=1), $C_{2-40}$ alkoxyalkyl (for n=1), $C_{1-40}$ alkylene (for n=2), $C_{3-40}$ cycloalkylene (for n=2), or $C_{6-40}$ arylene (for n=2).

The term "$C_{1-40}$ alkyl" as used in the present invention denotes branched and unbranched alkyl groups with 1 to 40 carbon atoms. Preferred are alkyl groups with 1 to 12 carbon atoms. Examples include: methyl, ethyl, n-propyl, iso-propyl, n-butyl, iso-butyl, sec-butyl, tert-butyl, n-pentyl, iso-pentyl, neo-pentyl or hexyl, heptyl, octyl, decyl, dodecyl. The definitions propyl, butyl, pentyl hexyl, heptyl, octyl, decyl and dodecyl include all possible isomeric forms of the groups in question. Thus, for example, propyl includes n-propyl and iso-propyl, butyl includes iso-butyl, sec-butyl and tert-butyl etc. Unless otherwise stated, the alkyl groups may be substituted by one or more groups.

The term "$C_{3-40}$ alkenyl" as used in the present invention denotes branched and unbranched alkenyl groups with 3 to 40 carbon atoms. Preferred are alkenyl groups with 3 to 5 carbon atoms. Examples include: propenyl, butenyl, pentenyl, or hexenyl. Unless otherwise stated, the definitions propenyl, butenyl, pentenyl and hexenyl include all possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

The term "$C_{3-40}$ cycloalkyl" as used in the present invention denotes cyclic alkyl groups with 3 to 40 carbon atoms. Examples include: cyclopropyl, cyclobutyl, cyclopentyl or cyclohexyl. Unless otherwise stated, the cycloalkyl groups may be substituted by one or more groups, preferably selected from methyl, ethyl, iso-propyl, tert-butyl, hydroxyl, fluorine, chlorine, bromine and iodine.

The term "$C_6$-$C_{40}$ aryl" as used in the present invention denotes aromatic ring systems with 6 to 40 carbon atoms. Examples include: phenyl, naphthyl and anthracenyl, the preferred aryl group being phenyl and napthyl. Unless otherwise stated, the aromatic groups may be substituted by one or more groups preferably selected from hydroxyl, alkoxy, such as methoxy or ethoxy, fluorine, chlorine, bromine, iodine and nitro.

The term "$C_{7-40}$ aralkyl" as used in the present invention denotes branched and unbranched alkyl groups with 1 to 30 carbon atoms which are substituted by an aromatic ring system with 6 or 10 carbon atoms. Examples include: benzyl, 1- or 2-phenylethyl. Unless otherwise stated, the aralykyl groups may be substituted by one or more groups preferably selected from hydroxyl, fluorine, chlorine, bromine and iodine.

The term "$C_{2-40}$ alkoxyalkyl" as used in the present invention refers to an alkoxy group covalently attached to an alkyl group, wherein the alkoxyalkyl group comprises the total number of 2 to 40 carbon atoms. The alkoxy group contains from 1 to 12, preferably from 1 to 6 carbon atoms. The alkoxy group may be substituted with one or more hydroxyl groups or with one or more halogen atoms. Examples of alkoxyalkyl groups include: ethoxyethyl, butoxymethyl, butoxybutyl, isopropoxy, pentoxymethyl, and hexoxymethyl.

The term "$C_{1-40}$ alkylene" as used in the present invention denotes branched and unbranched alkylene groups with 1 to 40 carbon atoms. Preferred are alkylene groups with 1 to 12 carbon atoms. Examples include: methylene, ethylene, propylene, butylene, pentylene, hexylene, heptylene, octylene, decylene, dodecylene. Unless otherwise stated, the alkylene groups may be substituted by one or more groups preferably selected from methyl, ethyl, iso-propyl, tert-butyl, hydroxy, fluorine, chlorine, bromine and iodine.

The term "$C_{3-40}$ cycloalkylene" as used in the present invention denotes cyclic alkylene groups with 3 to 40 carbon atoms. Examples include: cylopropylene, cyclobutylene, cyclopentylene or cyclohexylene. Unless otherwise stated, the cycloalkene groups may be substituted by one or more groups preferably selected from methyl, ethyl, iso-propyl, tert-butyl, hydroxy, fluorine, chlorine, bromine and iodine.

The term "$C_6$-$C_{40}$ arylene" as used in the present invention denotes divalent aromatic ring systems with 6 to 40 carbon atoms. Examples include: phenylene, naphthylene and anthracenylene, the preferred arylene group being phenylene and napthylene. Unless otherwise stated, the arylene groups may be substituted by one or more groups preferably selected from hydroxy, alkoxy, such as methoxy or ethoxy, fluorine, chlorine, bromine, iodine and nitro.

Preferred monohydric primary alcohols contain 2 to 18 carbon atoms, preferably 4 to 12 carbon atoms. Examples of preferred monohydric primary alcohols include methanol, ethanol, 1-propanol, 1-butanol, 2,2-dimethyl-1-propanol, 2-methyl-1-propanol, 2,2-dimethyl-1-propanol, 2-methyl-1-butanol, 3-methyl-1-butanol, 1-pentanol, 1-hexanol, 1-heptanol, and 1-octanol.

Preferred dihydric primary alcohols contain 2 to 18 carbon atoms, preferably 6 to 12 carbon atoms. Examples of preferred dihydric primary alcohols include: 1,4-butanediol, 1,5-pentanediol, 1,6-hexanediol, 1,7-heptanediol, and 1,8-octanediol.

In one embodiment of the present invention the at least one reagent is a primary mono- or diamine of general formula (IV)

[H$_2$N—]$_m$R$^3$     formula (IV)

wherein m is 1 or 2 and R$^3$ stands for $C_{1-40}$ alkyl (for n=1), $C_{3-40}$ alkenyl (for n=1), $C_{3-40}$ cycloalkyl (for n=1), $C_{6-40}$ aryl (for n=1), $C_{7-40}$ aralkyl (for n=1), $C_{2-40}$ alkoxyalkyl (for n=1), $C_{1-40}$ alkylene (for n=2), $C_{3-40}$ cycloalkylene (for n=2), or $C_{6-40}$ arylene (for n=2).

In another embodiment of the present invention the at least one reagent is a primary mono- or dithiol of general formula (V),

[HS—]$_o$R$^4$     formula (V)

wherein o is 1 or 2 and R$^4$ stands for $C_{1-40}$ alkyl (for n=1), $C_{3-40}$ alkenyl (for n=1), $C_{3-40}$ cycloalkyl (for n=1), $C_{6-40}$ aryl (for n=1), $C_{7-40}$ aralkyl (for n=1), $C_{2-40}$ alkoxyalkyl (for n=1), $C_{1-40}$ alkylene (for n=2), $C_{3-40}$ cycloalkylene (for n=2), or $C_{6-40}$ arylene (for n=2).

The terms "$C_{1-40}$ alkyl", "$C_{3-40}$ alkenyl", "$C_{3-40}$ cycloalkyl", "$C_{6-40}$ aryl", "$C_{7-40}$ aralkyl", "$C_{2-40}$ alkoxyalkyl", "$C_{1-40}$ alkylene", "$C_{3-40}$ cycloalkylene", and "$C_{6-40}$ arylene" are defined as given above.

In one embodiment of the invention, mixtures of hydroxyl-containing compounds and amine-containing compounds, or mixtures of hydroxyl-containing compounds and thiol-containing compounds, or mixtures of amine-containing compounds and thiol-containing compounds or mixtures of hydroxyl-containing compounds, amine-containing compounds and thiol-containing compounds are used as reagents in step ii) of the second process of the present invention.

2-cyanoacetic acid esters are preferably formed in the second process of the present invention, because these compounds are valuable starting materials for the production 2-cyanoacrylate monomers.

Preferred 2-cyanoacetic acid esters produced in the second process of the present invention are represented by general formula (VI),

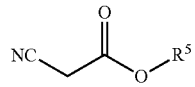

formula (VI)

wherein R$^5$ stands for a substituted or unsubstituted, branched or linear alkyl, alkenyl, cycloalkyl, aryl, aralkyl or alkoxyalkyl group. If said groups are in substituted form, the substituents are preferably one or more of methyl, ethyl, iso-propyl, tert-butyl, hydroxy, fluorine, chlorine, bromine and iodine plus optionally one or more ether oxygen atoms. If R$^5$ is an alkyl residue, then it preferably contains 1 to 16 carbon atoms, especially preferably 1 to 8 carbon atoms. If R$^5$ is a cycloalkyl residue, it preferably has 3 to 8 carbon atoms. R$^5$ preferably stands for a methyl, ethyl, n-propyl, isopropyl, n-butyl, isobutyl, pentyl, hexyl, heptyl, octyl, allyl, methallyl, crotyl, propargyl, cyclohexyl, benzyl, phenyl, cresyl, 2-chloroethyl, 3-chloropropyl, 2-chlorobutyl, trifluoroethyl, 2-methoxyethyl, 3-methoxybutyl and 2-ethoxyethyl or triethylene glycol monomethyl ether group.

The high selectivity of step i) of the second process of the present invention is of particular importance for step ii) and all subsequent steps of the second process of the present invention, especially in those cases, where the reaction mixture, containing 2-cyanoacetic acid anhydride, is directly used in step ii) of the second process of the present invention without any further purification. By producing 2-cyanoacetic acid anhydride selectively in step i) the number of possible by-products formed in step ii) and step iii) is limited and 2-cyanoacetic acid esters, 2-cyanoacetic acid amides and/or 2-cyanoacetic acid thioesters can be obtained in high yields and high purities For example, the second process of the present invention allows producing n-octyl cyanoacetate in 96% yield and 95% purity (based on the amount of alcohol added), and 3-methoxybutyl cyanoacetate in 95% yield and 95% purity (based on the amount of alcohol added).

In order to minimize the formation of undesired by-products which are difficult to remove it is preferred that a mixture is prepared in step ii) of the second process of the present invention which comprises the reagent and 2-cyanoacetic acid anhydride in a molar ratio from 0.4:1 to 1.8:1, preferably from 0.8 to 1.4, and more preferably from 0.9 to 1.1.

To accelerate the formation of the desired product in the second process of the present invention, it is preferred that the at least one reagent is added in step ii) in the presence of at least one catalyst, wherein the catalyst is capable of catalyzing the formation of 2-cyanoacetic acid esters, 2-cyanoacetic acid amides and/or 2-cyanoacetic acid thioesters.

In the present invention a catalyst is regarded as being capable of catalyzing the formation of 2-cyanoacetic acid ester, 2-cyanoacetic acid amides and/or 2-cyanoacetic acid thioesters, if said catalyst accelerates the formation of said compounds in comparison to an identical process under identical conditions, where the aforementioned catalyst is not present in the reaction mixture.

Suitable catalysts for the second process of the present invention include strong acids, such as sulfonic acids, like aromatic sulfonic acids and salts thereof, oxides, hydrides, hydroxides, carbonates, carboxylates, alkoxides, amines, such as pyridine or derivatives thereof, alkali or alkaline earth metals as well as basic metal oxides such as zinc oxides, salts of weak acids such as lithium stearate and organotitanium, organoaluminums and organotins, such as tetraoctyltitanate and mixtures thereof. Other preferred catalysts include, for example, poly(4-vinyl pyridines).

The concentration of the at least one catalyst should preferably be between 0.1 and 20 wt.-%, more preferably between 0.5 and 10 wt.-%, and particularly preferably between 0.6 and 3 wt.-%, based on the total amount of 2-cyanoacetic anhydride in the reaction mixture of step ii) of the second process of the present invention.

As noted above, the reaction temperature of step iii) of the second process of the present invention is in the range of −20° C. to 80° C., preferably in the range of 0° C. to 70° C., and more preferably in the range of 15° C. to 60° C. Depending on the reactivity of the at least one reagent used in step ii) of the second process of the present invention, the reaction time can vary, e.g. from 30 seconds to 96 hours, wherein reaction times of 1 hour to 10 hours, such as reaction times of 1.5 hours to 5 hours are particularly preferred.

As the first process, the second process of the present invention can be carried out in a continuous or batch manner.

In an alternative embodiment, the second process of the present invention is carried out continuously in a flow-through reactor, wherein the reaction mixture of the second process flows continuously through the flow-through reactor.

Due to cost efficiency reasons, it is particular preferably that all steps of the second process of the present invention are carried out in the same batch-type reactor or in the same flow-through reactor. By using only one batch-type or flow-through reactor, the 2-cyanoacetic acid anhydride formed in step i) of the second process of the present invention can be directly converted in step ii) and step iii) without any additional purification step.

In one embodiment, the second process of the present invention comprises the additional step iv) of isolating the formed 2-cyanoacetic acid ester, 2-cyanoacetic acid amide and/or 2-cyanoacetic acid thioester by a process selected from the group consisting of extraction, crystallization, chromatography, distillation and co-distillation and combinations thereof. If a solid catalyst was used in the second process of the present invention, said catalyst can be simply filtered out.

Preferably the product of the second process is isolated by removing the at least one organic solvent under reduced pressure and redissolving the residue in a suitable solvent, such as methylene chloride, ethyl acetate or mixtures thereof. The resulting solution can be washed, preferably repeatedly, with water and/or an aqueous solution of sodium hydrogen carbonate. Afterwards the organic phase can be separated and removed under reduced pressure to obtain 2-cyanoacetic acid ester, 2-cyanoacetic acid amide and/or 2-cyanoacetic acid thioester.

The organic solvents of the first and second process of the present invention can be selected from ketones, esters, hydrocarbons, halogenated hydrocarbons, nitriles, amides and ethers.

One preferred organic solvent for the first and second process of the present invention is acetonitrile, because, acetonitrile (compared to other solvents) is capable of accelerating the rate of reaction in the first and second process of the present invention.

Further preferred solvent include mixtures of toluene, THF, methylene chloride, and ethyl acetate. The combination of solvents is also advantageous in that it allows the separation of water from solvent in a Barrett or Dean-Stark distillation trap to be sharp and allowing nearly all the solvent to be returned to the reaction vessel. Other solvents such as xylene, cyclohexane, dichloromethane and chloroform, or water soluble solvents as tetrahydrofuran, dioxane, ethanol or propanol can also be used, however, the water soluble solvents being less preferred, since they are not suitable if the final product is to be separated and purified by washing procedures with aqueous solutions.

EXAMPLES

Example 1

First Process

To a solution of trifluoroacetic acid anhydride (19.95 g, 95 mmol) in acetonitrile (30 ml) was added 2-cyanoacetic acid (19.38 g, 228 mmol). The mixture was stirred for 5h under a nitrogen atmosphere at 22° C. The resulting yellow solution was reduced in vacuo to afford 18.6 g of a yellow oil. By NMR analysis the yellow oil was identified as a 10:1:6 mixture a of 2-cyanoacetic anhydride: 2-cyanoacetic trifluoroacetic anhydride: 2-cyanoacetic acid.

Second Process

The yellow oil of the first process was dissolved in dry acetonitrile (20 mL) and added dropwise to a mixture of 3-methoxybutanol (7.6 g, 73 mmol) and poly(4-vinyl pyridine) (13 g, 124 mmol) as a catalyst at 50° C. The resulting mixture was stirred for 2 h at 50° C. The solvents were removed under reduced pressure and the resulting residue was dissolved in methylene chloride (100 mL) and filtered. The filter cake was washed with a 1:1 mixture (50 mL) of methylene chloride and ethyl acetate and the combined organic phase was washed with sat. aq. $NaHCO_3$ and brine (50 mL each) and then dried over $MgSO_4$. The solvents and volatile components were removed under reduced pressure to afford 11.9 (95%) g of 3-methoxybutyl 2-cyanoacetic ester (purity of 95%, as determined by GC).

$^1$H NMR: 4.31 (2H, t, J=7.1), 3.91 (2H, s), 3.57 (1H, qt, J=6.1, J=3.8), 3.4 (s, 3H), 2.0 (2H, td, J=7.1, J=3.8), 1.133 (3H, d, J=6.1).

Example 2

One Pot Process (Comprising the First and Second Process of the Present Invention)

To a solution of TFAA (22.4 g, 107 mmol) in acetonitrile (100 mL) was added 2-cyanoacetic acid (20 g, 235 mmol). The mixture was stirred for 3 h at 22° C. under a dry atmosphere. The formation of the 2-cyanoacetic anhydride was verified by NMR (s, 3.85 ppm). A solution of 3-methoxybutanol (10 g, 96 mmol) in acetonitrile (30 mL) was added dropwise (10 min). A slight exotherm was noted. The pale yellow mixture was stirred at 22° C. for 3 h. The solvents were removed in vacuo and the resulting yellow oil taken up in 100 mL of methylene chloride. The solution was neutralized by the addition of aq. sat. sodium bicarbonate. The aqueous layer was separated and extracted with 50 mL of methylene chloride. The combined organics were dried over $MgSO_4$ and reduced to afford a pale yellow liquid, 15 g (91%) which had a purity of 98.4% by GC.

$^1$H NMR: 4.31 (2H, t, J=7.1), 3.91 (2H, s), 3.57 (1H, qt, J=6.1, J=3.8), 3.4 (s, 3H), 2.0 (2H, td, J=7.1, J=3.8), 1.133 (3H, d, J=6.1).

Comparative Example 1

Dichloromethane Reaction Mixture Containing Trifluoroacetic Acid Anhydride and 2-cyanoacetic Acid in a Molar Ratio of 1:1

To a solution of trifluoroacetic acid anhydride (26 g, 123 mmol) in dichloromethane (30 mL) was added 2-cyanoacetic acid (10 g, 118 mmol). The mixture was stirred for 15 min under a nitrogen atmosphere at 22° C. and NMR showed one peak (3.95 ppm) The resulting yellow solution was added dropwise over 30 mins to a solution of 6-hydroxy-methylhexanoate (17.1 g 117 mmol) in ethyl acetate (250 mL). The mixture was stirred at 22° C. for 3 h. The solution was neutralized with sat aq. sodium bicarbonate. The aqueous layer was separated and back extracted with 100 mL of ethyl acetate. The combined organics were dried over magnesium sulfate and reduced to afford 22.8 g of a clear liquid. This was distilled under vacuum (0.03 mbar) to afford 2 fractions—5.7 g of trifluoroacetic acid ester and 16 g of the cyanoacetic acid ester of 6-hydroxy-methylhexanoate (64%).

Cyanoacetic acid ester of 6-hydroxy-methylhexanoate: $^1$H NMR: 4.19 (2H, t, J=7.1), 3.66 (s, 3H), 3.49 (2H, s), 2.33 (2H, t, J=7.4), 1.73 (2H, tt, J=7.4, J=7.1), 1.55 (2H, tt, J=7.5, J=7.4), 1.43 (2H, tt, J=7.5, J=7.4).

Trifluoroacetic acid ester of 6-hydroxy-methylhexanoate: $^1$H NMR: 4.36 (2H, t, J=7.1), 3.66 (s, 3H), 2.34 (2H, t, J=7.4), 1.73 (2H, tt, J=7.4, J=7.1), 1.55 (2H, tt, J=7.5, J=7.4), 1.43 (2H, tt, J=7.5, J=7.4).

Comparative Example 2

Acetonitrile Reaction Mixture Containing Trifluoroacetic Acid Anhydride and 2-cyanoacetic Acid in a Molar Ratio of 1:1

To a solution of trifluoroacetic acid anhydride (11.2 g, 53.2 mmol) in acetonitrile (30 mL) was added 2-cyanoacetic acid (4.5 g, 53.2 mmol). The mixture was stirred for 3 h at 22° C. under a dry atmosphere. A solution of 3-methoxybutanol (5.0 g, 48.5 mmol) in dry acetonitrile (20 mL) was added dropwise. The mixture was stirred for at 22° C. for 3 h. The solvents were removed in vacuo and the resulting yellow oil taken up in 50 mL of methylene chloride. The solution was neutralized by the addition of aq. sat. sodium bicarbonate. The aqueous layer was separated and extracted with 50 mL of methylene chloride. The combined organics were dried with magnesium sulfate and reduced in vacuo to afford 8.1 g of a pale yellow liquid. GCMS revealed this to be a 78.5/21.5% mixture of 3-methoxybutyl cyanoacetate and 3-methoxybutyl trifluoroacetate.

What is claimed is:

1. A process for producing 2-cyanoacetic acid anhydride, comprising the steps of:
   a) preparing a reaction mixture, containing as reactants 2-cyanoacetic acid, and at least one $C_{4-20}$ carboxylic acid anhydride in at least one organic solvent, wherein the molar ratio of 2-cyanoacetic acid to $C_{4-20}$ carboxylic acid anhydride in said reaction mixture is greater than 1.5:1; and
   b) subjecting the reaction mixture to a temperature of 0° C. to 100° C. to form 2-cyanoacetic acid anhydride.

2. The process of claim 1, wherein the molar ratio of 2-cyanoacetic acid to $C_{4-20}$ carboxylic acid anhydride in said reaction mixture is from 2:1 to 3:1.

3. The process of claim 1, wherein the $C_{4-20}$ carboxylic acid anhydride is a symmetrical $C_{4-20}$ carboxylic acid anhydride.

4. The process of claim 1, wherein the $C_{4-20}$ carboxylic acid anhydride is selected from symmetrical carboxylic acid anhydrides of formula (I),

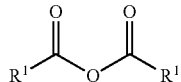

formula (I)

wherein $R^1$ represents $C_{1-9}$-halogenoalkyl, or represents phenyl which is substituted by at least one substituent selected from fluorine, chlorine, bromine, cyano and/or nitro.

5. The process of claim 1, wherein the $C_{4-20}$ carboxylic acid anhydride is selected from compounds of formula (III),

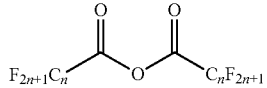

formula (III)

wherein each n, independently, is an integer from 1 to 5.

6. The process according to claim 1, wherein the $C_{4-20}$ carboxylic acid anhydride is trifluoroacetic acid anhydride.

7. The process according to claim 1, wherein the temperature in step b) is from 10° C. to 40° C.

8. The process of claim 1, comprising the additional step c) of concentrating 2-cyanoacetic acid anhydride by removing at least a part of the organic solvent.

9. A process for producing 2-cyanoacetic acid esters, 2-cyanoacetic acid amides and/or 2-cyanoacetic acid thioesters, comprising the steps of:
   i) carrying out a process of claim 1 to prepare a reaction mixture containing 2-cyanoacetic acid anhydride in an organic solvent;
   ii) adding at least one reagent to the reaction mixture, wherein said reagent is selected from the group consisting of hydroxyl-containing compounds, amine-containing compounds, and thiol-containing compounds; and
   iii) subjecting said mixture to a temperature of –20° C. to 80° C. to form 2-cyanoacetic acid esters, 2-cyanoacetic acid amides and/or 2-cyanoacetic acid thioesters.

10. The process of claim 9, wherein the reagent is a monohydric or dihydric primary alcohol.

11. The process of claim 10, wherein the monohydric or dihydric primary alcohol has general formula (II),

[HO—]$_n$R$^2$   formula (II)

wherein n is 1 or 2 and $R^2$ stands for $C_{1-40}$ alkyl (for n=1), $C_{3-40}$ alkenyl (for n=1), $C_{3-40}$ cycloalkyl (for n=1), $C_{6-40}$ aryl (for n=1),
$C_{7-40}$ aralkyl (for n=1), $C_{2-40}$ alkoxyalkyl (for n=1), $C_{1-40}$ alkylene (for n=2), $C_{3-40}$ cycloalkylene (for n=2), or $C_{6-40}$ arylene (for n=2).

12. The process according to claim 9, wherein the molar ratio of reagent to 2-cyanoacetic acid anhydride in step ii) is from 0.4:1 to 1.8:1.

13. The process according to claim 9, wherein the at least one reagent is added in step ii) in the presence of at least one catalyst, wherein the catalyst is capable of catalyzing the formation of 2-cyanoacetic acid esters, 2-cyanoacetic acid amides and/or 2-cyanoacetic acid thioesters.

14. The process according to claim 9, wherein the temperature in step iii) is from 0° C. to 40° C.

15. The process according to claim 1, wherein the organic solvent is selected from ketones, esters, hydrocarbons, halogenated hydrocarbons, nitriles, amides and ethers.

* * * * *